United States Patent
Campin

(10) Patent No.: US 6,568,808 B2
(45) Date of Patent: May 27, 2003

(54) EYE TRACKER CONTROL SYSTEM AND METHOD

(75) Inventor: John Alfred Campin, Orlando, FL (US)

(73) Assignee: Alcon Universal Ltd., Hunenberg (CH)

( * ) Notice: Subject to any disclaimer, the term of this patent is extended or adjusted under 35 U.S.C. 154(b) by 35 days.

(21) Appl. No.: 09/842,357

(22) Filed: Apr. 25, 2001

(65) Prior Publication Data

US 2002/0030789 A1 Mar. 14, 2002

Related U.S. Application Data

(60) Provisional application No. 60/199,637, filed on Apr. 25, 2000.

(51) Int. Cl.[7] ................................................. A61B 3/14
(52) U.S. Cl. ......................................................... 351/209
(58) Field of Search ............................... 351/200, 205, 351/206, 208, 209, 210, 221, 246

(56) References Cited

U.S. PATENT DOCUMENTS

| | | | | |
|---|---|---|---|---|
| 4,856,891 A | * | 8/1989 | Pflibsen et al. .............. | 351/206 |
| 5,410,376 A | * | 4/1995 | Cornsweet et al. .......... | 351/209 |
| 5,422,690 A | * | 6/1995 | Rothberg et al. ............ | 351/209 |
| 5,865,832 A | * | 2/1999 | Knopp et al. | |
| 5,980,513 A | * | 11/1999 | Frey et al. .................... | 351/209 |
| 6,027,216 A | * | 2/2000 | Guyton et al. ............... | 351/200 |
| 6,210,401 B1 | * | 4/2001 | Lai .............................. | 351/209 |
| 6,299,307 B1 | * | 10/2001 | Oltean et al. ................. | 351/210 |
| 6,394,999 B1 | * | 5/2002 | Williams et al. ............. | 351/212 |

FOREIGN PATENT DOCUMENTS

WO          99/27412          6/1999

* cited by examiner

*Primary Examiner*—Marvin M. Lateef
*Assistant Examiner*—John R. Sanders
(74) *Attorney, Agent, or Firm*—Allen, Dyer, Doppelt, Milbrath & Gilchrist, P.A.

(57) ABSTRACT

A system and method for controlling an eye movement tracker includes monitoring a plurality of eye positions by following a feature using the tracker. An optical beam is sent into the eye, and an intensity of a reflected beam from the eye is sensed at each position. If the intensity of the reflected beam fluctuates from a predetermined acceptable intensity range, the tracker is returned to a frozen position. The frozen position comprises a most recent position at which the intensity lay within the intensity range. The tracker is also frozen if the noise in the signal exceeds a predetermined acceptable maximum noise level and for counting a number of times the tracker is frozen. The procedure is aborted if the tracker is frozen repeatedly and for a time exceeding a predetermined maximum acceptable time.

21 Claims, 3 Drawing Sheets

EYE TRACKER CONTROL SYSTEM AND METHOD

CROSS-REFERENCE TO RELATED APPLICATIONS

This application claims priority from commonly owned provisional application Ser. No. 60/199,637, filed Apr. 25, 2000, "Detecting and Responding to Objects Obscuring Tracker Field of View during Refractive Surgery."

BACKGROUND OF THE INVENTION

1. Field of the Invention

The present invention relates to systems and methods for performing eye tracking, and, more particularly, to such systems and methods for controlling the functions of an eye tracker during measurement and correction of aberrations in a visual system.

2. Description of Related Art

Optical systems having a real image focus can receive collimated light and focus it at a point. Such optical systems can be found in nature, e.g., human and animal eyes, or can be manmade, e.g., laboratory systems, guidance systems, and the like. In either case, aberrations in the optical system can affect the system's performance. By way of example, the human eye will be used to explain this problem.

A perfect or ideal eye diffusely reflects an impinging light beam from its retina through the optics of the eye, which includes a lens and a cornea. For such an ideal eye in a relaxed state, i.e., not accommodating to provide near-field focus, reflected light exits the eye as a sequence of plane waves. However, an eye typically has aberrations that cause deformation or distortion of reflected light waves exiting the eye. An aberrated eye diffusely reflects an impinging light beam from its retina through its lens and cornea as a sequence of distorted wavefronts.

There are a number of technologies that attempt to provide the patient with improved visual acuity. Examples of such technologies include remodeling of the cornea using refractive laser surgery or intra-corneal implants, adding synthetic lenses to the optical system using intra-ocular lens implants, and precision-ground spectacles. In each case, the amount of corrective treatment is typically determined by placing spherical and/or cylindrical lenses of known refractive power at the spectacle plane (approximately 1.0–1.5 cms anterior to the cornea) and literally asking the patient which lens or lens combination provides the clearest vision. This is an imprecise measurement of true distortions in the reflected wavefront because (1) a single spherocylindrical compensation is applied across the entire wavefront; (2) vision is tested at discrete intervals (i.e., diopter units) of refractive correction; and (3) subjective determination by the patient is made in order to determine the optical correction. Thus conventional methodology for determining refractive errors in the eye is substantially less accurate than the techniques now available for correcting ocular aberrations.

Various embodiments of a method and system for objectively measuring aberrations of optical systems by wavefront analysis have been disclosed in commonly owned application Ser. No. 09/566,668, "Apparatus and Method for Objective Measurement and Correction of Optical Systems Using Wavefront Analysis," filed May 8, 2000, which is hereby incorporated by reference herein. In this invention, an energy source generates a beam of radiation. Optics, disposed in the path of the beam, direct the beam through a focusing optical system (e.g., the eye) that has a rear portion (e.g., the retina) that provides a diffuse reflector. The beam is diffusely reflected back from the rear portion as a wavefront of radiation that passes through the focusing optical system to impinge on the optics. The optics project the wavefront to a wavefront analyzer in direct correspondence with the wavefront as it emerges from the focusing optical system. A wavefront analyzer is disposed in the path of the wavefront projected from the optics and calculates distortions of the wavefront as an estimate of ocular aberrations of the focusing optical system. The wavefront analyzer includes a wavefront sensor coupled to a processor that analyzes the sensor data to reconstruct the wavefront to include the distortions thereof.

A perfectly collimated light beam (i.e., a bundle of parallel light rays, here a small-diameter, eye-safe laser beam) incident on a perfect, ideal emmetropic eye, focuses to a diffraction-limited small spot on the retina. This perfect focusing is true for all light rays passing through the entrance pupil, regardless of position. From the wavefront perspective, the collimated light represents a series of perfect plane waves striking the eye. The light emanates from an illuminated spot on the retina as wavefronts exiting as a series of perfect plane waves, which are directed onto a wavefront analyzer for measuring distortions from ideality.

One problem with the sensing of such wavefront data is the natural eye movement that occurs during an exposure. Multiple exposures may be used to check for improper eye alignment or eye movement during individual exposures. However, often eye movement during exposures cannot be analyzed successfully by acquiring multiple exposures.

Following measurement of the eye aberrations, a patient may elect to undergo corrective laser surgery, performed, for example, by laser ablation of portions of the corneal surface to achieve a calculated shape for improving visual acuity. In this case it is also desirable to account for eye movement during surgery while delivering laser shots to the cornea. Given an eye tracker apparatus as part of the ablation system, it is also desirable to account for any object that may temporarily obscure the field of vision of the tracker.

SUMMARY OF THE INVENTION

It is therefore an object of the present invention to provide a system and method for tracking eye movement during measurement of ocular aberrations.

It is a further object to provide a system and method for tracking eye movement during laser surgery to correct ocular aberrations.

It is another object to provide a system and method for detecting an object obscuring a field of view of a tracking system.

It is an additional object to provide such a system and method for responding to the obscuring object.

It is yet a further object to provide such a system and method for aborting a surgical procedure under certain predetermined conditions of the tracking system.

It is yet another object to provide such a system and method for temporarily halting a laser surgical procedure during an obscuring of the tracker system.

These and other objects are achieved by the present invention, a system and method for controlling an eye movement tracker. The method comprises the step of monitoring a plurality of positions of an eye at a predetermined rate by following a predetermined eye feature using the tracker. An optical beam is sent into the eye, and an intensity of a reflected beam from the eye is sensed at each position.

If the intensity of the reflected beam fluctuates from a predetermined acceptable intensity range, the tracker is returned to a frozen position. The frozen position comprises a most recent position at which the intensity lay within the intensity range.

The method further comprises steps for freezing the tracker if the noise in the signal exceeds a predetermined acceptable maximum noise level and for counting a number of times the tracker is frozen. The procedure is aborted if the tracker is frozen repeatedly and for a time exceeding a predetermined maximum acceptable time.

The system of the present invention comprises means for performing the above-recited steps, including a processor and software means for performing the required calculations.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
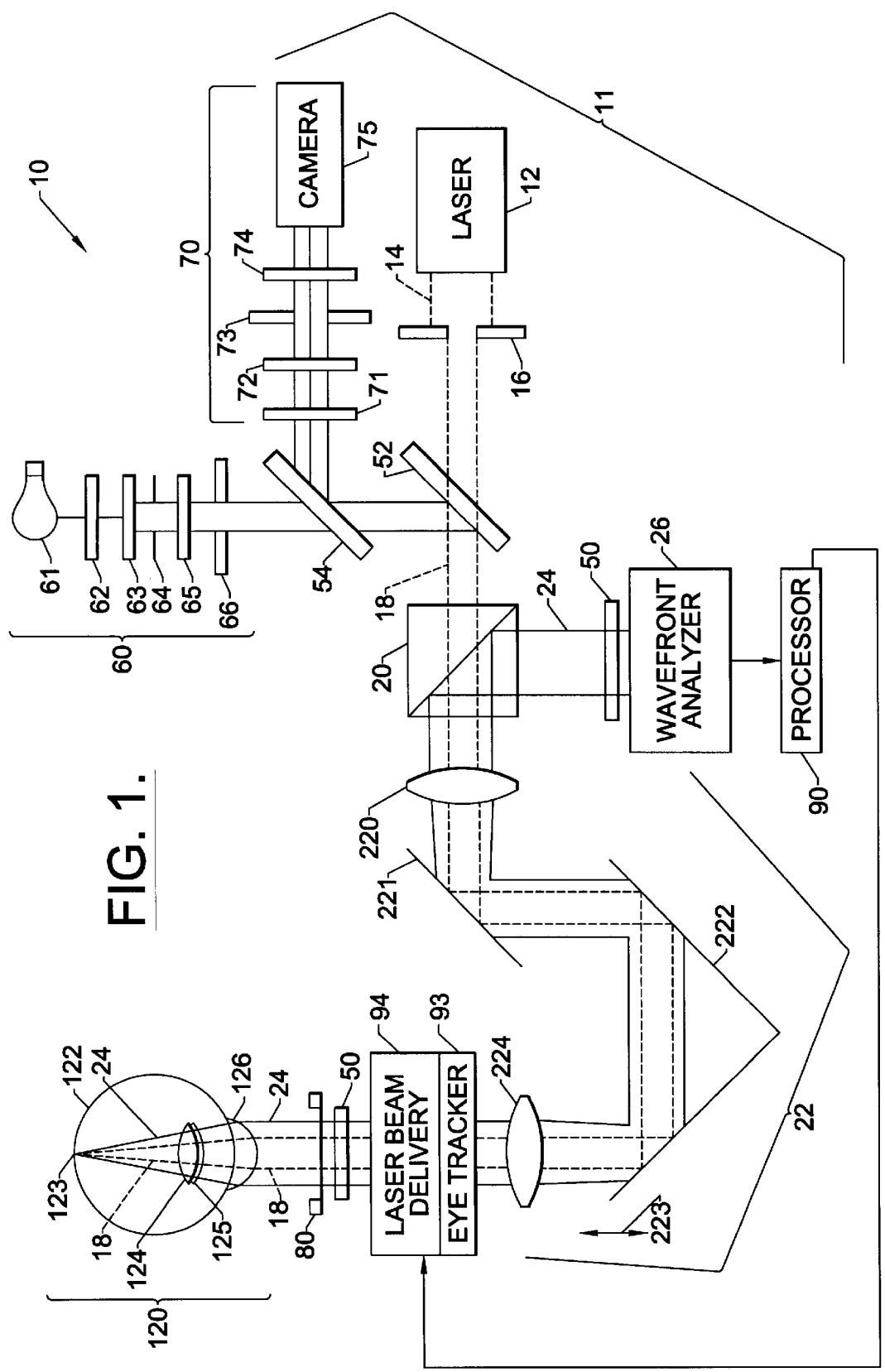
FIG. 1 is a schematic diagram of the eye measurement and aberration correction system.
Figure 2:
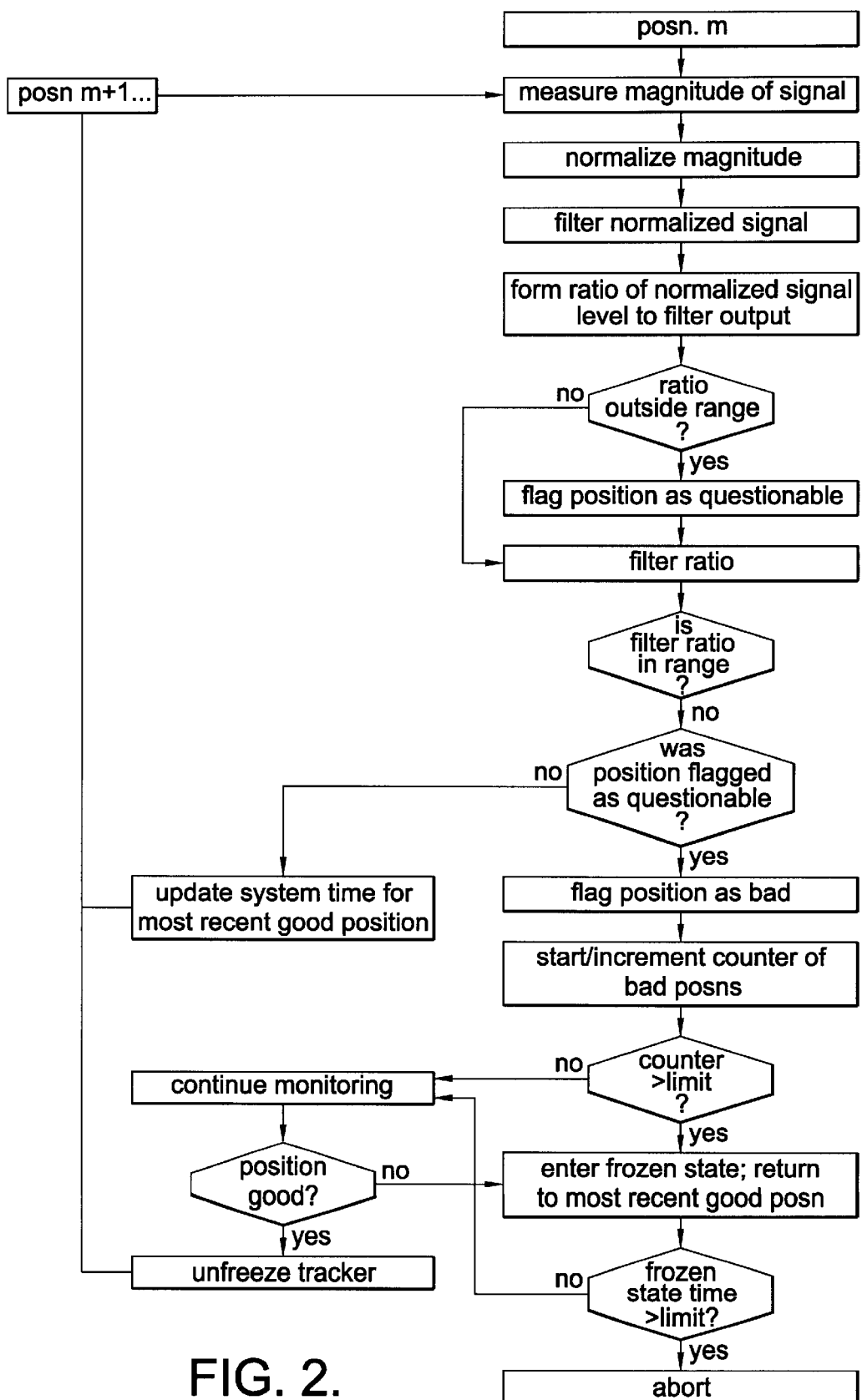
FIG. 2 is a flow diagram of the tracker control system of the present invention.
Figure 3:
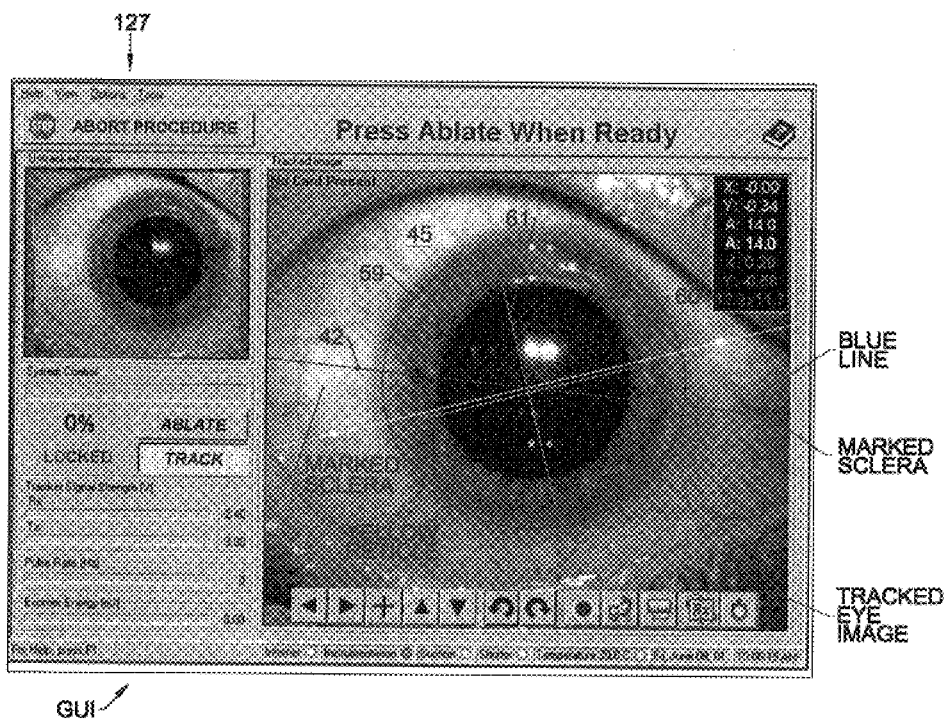
FIG. 3 illustrates an exemplary graphical user interface with a positioning reticle thereon.

A description of the preferred embodiments of the present invention will now be presented with reference to FIGS. 1–3.

During the measurement phase of an ocular correction procedure, multiple exposures may be used to check for improper eye alignment or eye movement during individual exposures. If eye movement during exposures cannot be analyzed successfully by acquiring multiple exposures, then the system 10 can be augmented by the addition of an eye tracker 94, illustrated with reference to FIG. 1. One possible placement of the eye tracker 94 is herein illustrated. However, it is to be understood that the eye tracker 94 could be placed elsewhere within the system 10. One such eye tracker is disclosed in U.S. Pat. No. 5,980,513, commonly owned with the present invention, and the disclosure of which is incorporated herein by reference. In this way, wavefront analysis may be performed even during a limited amount of eye motion.

In a possible laser ablation procedure using system 10, information regarding the amount of corneal material will have been calculated using the information gleaned from the measurement procedure. The procedure uses a laser beam delivery system 93 that is under control of the eye tracking system 94. The laser beam delivery system 93 and the eye tracker 94 are placed in line with the optical axis of the system 10. The eye tracker 94 allows the system 10 to respond to unwanted eye motion.

The ability of the tracking system 94 to perform well is a direct function of how well the tracker can "see" the features it is tracking. If the tracking system 94 is watching the pupil boundary, for example, the ability of the tracking system 94 to maintain a constant track point on the eye 120 is impaired as soon as any of the pupil boundary is obscured. Obscuration of the pupil boundary may occur in either or both of the following ways:

1. The eye 120 moves sufficiently that the eyelid or another part of the face hides the pupil. An example includes the eye temporarily rolling upward toward the top of the head.
2. An object is inserted into the tracker-pupil path. Examples include such objects as a finger, a surgical instrument, and a microkeratome.

If a refractive surgical procedure is ongoing and the tracker performance is impaired in one of these ways, or in another way, then it is likely that the ablation will not be optimally positioned on the eye.

In a particular solution, the tracker could simply respond to an obscuration by aborting the procedure. A preferred embodiment of the present invention addresses this problem with a robust, automated method for detecting such an obscuration and responding by temporarily halting the procedure. In a case in which a predetermined set of circumstances is present, a complete abort is performed. The method comprises the following steps:

1. The tracking system computes and maintains metrics that define the track quality on a sample-by-sample basis.
2. If a poor track quality is determined for a sample, then the system logs the tracker geometry and other key tracker parameters from the most recent good-quality sample.
3. If a predetermined number of consecutive poor-track-quality samples are detected, then the tracker changes into a mode termed "coast." Typically more than one poor-quality sample is required in order to make the system more robust to noise.
4. In coast mode, the tracker geometry is restored to the geometry from the most recent good-quality sample, and frozen. The tracker data from the eye continue to be monitored, but the system does not respond to these data until track quality again becomes acceptable.
5. Once the track quality returns to acceptable, the full tracking system is reactivated, and tracker geometry is unfrozen, and the tracker quality monitoring continues.

Additional logic in the system 94 provides the following responses:

1. If the tracker remains in coast mode for a time exceeding a predetermined period, the procedure is aborted. Coast mode preferably handles short-term obscurations as listed above.
2. If the tracker rapidly and repeatedly enters and leaves coast mode, the procedure is aborted. This is considered unacceptable behavior.

Track quality assessment comprises two parts:
1. Monitoring received signal levels
2. Monitoring the noise content of the signal Of these, (2) is performed relatively slowly (e.g., 10 Hz), and does not make use of the received signal levels. It also looks at the noise content within the signal. A high noise content typically implies poor track quality. If sufficiently high noise content is determined, the track is aborted and the operator is forced to reacquire the eye.

On the other hand, (1) runs at a higher rate (e.g., 200 Hz), monitors the received signal, and detects when an object is interfering with the path from the eye to the tracker. It is this functionality that facilitates the coast mode, the details of which are (see FIG. 2):

1. On a dwell-by-dwell basis (i.e., sequentially in time) the magnitude of the signal returning from the eye is measured.
2. This magnitude is normalized by a function of the tracker transmit/receive gain settings so that a system-setting-independent signal level is computed for the eye. In this way, changes in system gains are not misinterpreted as changes in the eye.
3. These normalized magnitudes are input to a low-pass filter. The output of this is, therefore, a smoothed, filtered estimate of recent signal magnitudes.
4. The current, normalized signal level is divided by the output of the low-pass filter from the previous dwell (i.e., the filter is not updated with current information before using the output; the output is used and then the input is updated).
5. If this ratio is greater than an upper threshold or less than a lower threshold, the current dwell is flagged as questionable. Note: Blocking the tracker path causes the lower threshold to be violated, while the insertion of a bright object such as a mirrored tool can result in the upper threshold's being exceeded.
6. The ratio of current normalized signal to low-pass filter output is itself fed into a second low-pass filter. The output of this is a filtered ratio.
7. If the current dwell is considered questionable, the filtered ratio is compared to the upper and lower thresholds in the same way as was done in (5). If the same threshold (upper or lower) is exceeded here, the current dwell is flagged as unsatisfactory.
8. If the preceding dwell was not unsatisfactory, the system time is logged so that we know when the most recent good dwell occurred.
9. A "bad sample" counter is started.
10. Each consecutive "bad" dwell results in the "bad sample" counter being incremented.
11. If the counter reaches a predetermined limit, the system state is changed to coast mode. If a good dwell occurs before this limit is reached, the counter is reset to zero and all monitoring functions continue as before the bad dwell(s) were detected.
12. If the system is set to coast mode, the tracker mirrors are repositioned to the locations corresponding to the preceding good dwell and held there while the signals continue to be monitored. If the excimer laser was firing, then this is inhibited.
13. If a "good" dwell is detected, the system leaves coast mode and continues as normal.
14. If the coast mode persists for more than a predetermined amount of time, the mode changes from coast to abort, and the procedure is interrupted. An appropriate message is displayed for the operator. Note: This time period is longer before the laser starts firing than during laser firing to permit the operator to manipulate the eye and instruments such as a microkeratome.
15. If the tracker rapidly and repeatedly enters and leaves coast mode, the procedure is aborted. This is considered unexpected behavior.

In another embodiment of the present invention, the tracking system detects a presence of a microkeratome in the tracker path. This is useful when the operator is positioning the microkeratome prior to cutting a flap in the cornea. It is preferable to position the microkeratome so that the ablation zone is totally within the boundaries of the cut. In order to achieve this, the operator needs to be able to position the limbus ring in a graphical user interface 127 (FIG. 3) over the patient's limbus so that a reticle indicating the ablation zone location is correctly positioned.

However, with a microkeratome in place, the limbus is obscured. This can be overcome by acquiring track data and positioning the limbus reticle prior to positioning the microkeratome. The tracker will go into coast mode while the microkeratome is moved into place and then automatically resumes tracking once the microkeratome is approximately in place and the pupil boundary is again visible. The ablation zone reticle still accurately indicates where the ablation will occur and can be used as an aid in positioning the microkeratome.

It will be seen by one of skill in the art that other embodiments and uses may be contemplated for the present invention. For example, the eye tracker monitoring system and method may be used in settings other than surgical sites, including such sites as for psychological and physiological testing applications.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for controlling an eye movement tracker comprising the steps of:
    monitoring a plurality of positions of an eye at a predetermined rate by following a predetermined eye feature using the tracker;
    sending an optical beam into the eye;
    sensing an intensity of a reflected beam from the eye at each position;
    if the intensity of the reflected beam fluctuates from a predetermined acceptable intensity range, returning the tracker to a frozen position comprising a most recent position at which the intensity lay within the intensity range;
    counting a number of times the tracker enters the frozen state; and
    if the number of times exceeds a predetermined maximum number, aborting the operation of the eye tracker.

2. The method recited in claim 1, further comprising the steps, following the returning step, of:
    continuing to sense the reflected beam; and
    maintaining the tracker at the frozen position until the intensity of the reflected beam is within the acceptable intensity range.

3. The method recited in claim 2, further comprising the step, following the maintaining step, of resuming the monitoring step when the intensity of the reflected beam is within the acceptable intensity range.

4. The method recited in claim 2, further comprising the steps of:
   timing a period during which the tracker is maintained in the frozen state; and
   if the period exceeds a predetermined maximum time period, aborting the operation of the eye tracker.

5. The method recited in claim 1, further comprising the steps of:
   monitoring a noise content of the reflected beam; and
   if the noise content exceeds a predetermined threshold, aborting the operation of the eye tracker.

6. The method recited in claim 5, wherein the noise content monitoring step is performed less frequently than the intensity sensing step.

7. The method recited in claim 1, wherein the intensity sensing step comprises normalizing a raw intensity magnitude relative to a setting of the tracker to form a normalized signal level for each position.

8. The method recited in claim 7, wherein the intensity sensing step further comprises filtering a raw intensity magnitude through a low-pass filter to form an output for each position.

9. The method recited in claim 8, further comprising the steps of:
   dividing the normalized signal level for a current position by the filter output of the preceding position to form a ratio; and
   if the ratio is outside a predetermined acceptable ratio range, considering the signal from the current position as questionable.

10. The method recited in claim 9, further comprising the steps of:
    filtering the ratio through a second low-pass filter to form a filtered ratio;
    if the filtered ratio is outside a predetermined acceptable filtered ratio range, considering the current position unacceptable.

11. The method recited in claim 1, further comprising the step, if the monitoring step is occurring during a laser-ablation procedure, of disabling laser firing while the tracker resides in the frozen position.

12. A system for controlling an eye movement tracker comprising:
    tracker means for monitoring a plurality of positions of an eye at a predetermined rate by following a predetermined eye feature using the tracker;
    means for sending an optical beam into the eye;
    means for sensing an intensity of a reflected beam from the eye at each position;
    if the intensity of the reflected beam fluctuates from a predetermined acceptable intensity range, means for returning the tracker to a frozen position comprising a most recent position at which the intensity lay within the intensity range;
    a counter for counting a number of times the tracker enters the frozen state; and
    means for aborting the operation of the eye tracker if the number of times exceeds a predetermined maximum number.

13. The system recited in claim 12, further comprising:
    continuing to sense the reflected beam; and
    means for maintaining the tracker at the frozen position until the intensity of the reflected beam is within the acceptable intensity range.

14. The system recited in claim 13, further comprising means for reactivating the tracker when the intensity of the reflected beam is within the acceptable intensity range.

15. The system recited in claim 13, further comprising:
    a timer for timing a period during which the tracker is maintained in the frozen state; and
    means for aborting the operation of the eye tracker if the period exceeds a predetermined maximum time period.

16. The system recited in claim 12, further comprising:
    means for monitoring a noise content of the reflected beam; and
    means for aborting the operation of the eye tracker if the noise content exceeds a predetermined threshold.

17. The system recited in claim 12, further comprising means for disabling laser firing while the tracker resides in the frozen position if the monitoring is occurring during a laser-ablation procedure.

18. A method for correcting aberrations in an eye comprising the steps of
    determining an optical path difference between a plane wave and a wavefront emanating from a region of a retina of an eye; and
    optically correcting for visual defects of the eye based on criteria comprising the optical path difference, to thereby cause the wavefront to approximate the shape of the plane wave;
    monitoring a plurality of positions of the eye at a predetermined rate during the correcting step by following a predetermined eye feature using an eye tracker;
    sending an optical beam into the eye;
    sensing an intensity of a reflected beam from the eye at each position;
    if the intensity of the reflected beam fluctuates from a predetermined acceptable intensity range, returning the tracker to a frozen position comprising a most recent position at which the intensity lay within the intensity range and halting the correcting step;
    counting a number of times the tracker enters the frozen state; and
    if the number of times exceeds a predetermined maximum number, aborting the operation of the eye tracker.

19. The method recited in claim 18, wherein the correcting step comprises performing a laser ablation procedure on a cornea of the eye.

20. A system for correcting aberrations in an eye comprising the steps of:
    means for determining an optical path difference between a plane wave and a wavefront emanating from a region of a retina of an eye; and
    means for optically correcting for visual defects of the eye based on criteria comprising the optical path difference, to thereby cause the wavefront to approximate the shape of the plane wave;
    an eye tracker for monitoring a plurality of positions of the eye at a predetermined rate during the correcting step by following a predetermined eye feature using an eye tracker;
    means for sending an optical beam into the eye; means for sensing an intensity of a reflected beam from the eye at each position;
    means for returning the tracker to a frozen position comprising a most recent position at which the intensity lay within the intensity range and halting the correcting means if the intensity of the reflected beam fluctuates from a predetermined acceptable intensity range;

a counter for counting a number of times the tracker enters the frozen state; and means for aborting the operation of the eye tracker if the number of times exceeds a predetermined maximum number.

21. The system recited in claim 20, wherein the correcting means comprises a laser system for performing an ablation procedure on a cornea of the eye.

* * * * *